(12) United States Patent
Xu

(10) Patent No.: US 8,552,359 B2
(45) Date of Patent: Oct. 8, 2013

(54) OPTICAL SPECTROSCOPY DEVICE FOR NON-INVASIVE BLOOD GLUCOSE DETECTION AND ASSOCIATED METHOD OF USE

(75) Inventor: Zhi Xu, Saint Louis, MO (US)

(73) Assignee: The Curators of the Univesity of Missouri, Saint Louis, MO (US)

( * ) Notice: Subject to any disclaimer, the term of this patent is extended or adjusted under 35 U.S.C. 154(b) by 685 days.

(21) Appl. No.: 12/729,886

(22) Filed: Mar. 23, 2010

(65) Prior Publication Data

US 2010/0252721 A1   Oct. 7, 2010

Related U.S. Application Data

(60) Provisional application No. 61/165,547, filed on Apr. 1, 2009.

(51) Int. Cl.
*G01N 33/48* (2006.01)

(52) U.S. Cl.
USPC .......................................... 250/226; 356/39

(58) Field of Classification Search
USPC ................. 250/226, 239; 362/296.05, 308, 362/154; 356/39–40, 436–440; 600/322, 600/310–319
See application file for complete search history.

(56) References Cited

U.S. PATENT DOCUMENTS

| | | | |
|---|---|---|---|
| 2,441,343 A | 5/1948 | Becker | |
| 3,621,268 A | 11/1971 | Friedrich et al. | |
| 3,910,701 A | 10/1975 | Henderson et al. | |
| 3,954,560 A | 5/1976 | Delafosse et al. | |
| 3,963,327 A | 6/1976 | Poirier | |
| 4,014,321 A | 3/1977 | March | |
| 4,632,559 A | 12/1986 | Brunsting | |
| 4,655,225 A | 4/1987 | Dahne et al. | |
| 4,781,195 A | 11/1988 | Martin | |
| 4,962,311 A | 10/1990 | Poisel et al. | |
| 4,997,769 A | 3/1991 | Lundsgaard et al. | |
| 5,009,230 A | 4/1991 | Hutchinson | |

(Continued)

FOREIGN PATENT DOCUMENTS

| CN | 1192665 | 9/1998 |
|---|---|---|
| CN | 2694097 Y | 4/2005 |

(Continued)

OTHER PUBLICATIONS

Office Action for U.S. Appl. No. 12/407,999 dated Apr. 6, 2012.

(Continued)

*Primary Examiner* — Seung C Sohn
(74) *Attorney, Agent, or Firm* — Thompson Coburn LLP

(57) ABSTRACT

An apparatus for concentrating light and associated method of use is disclosed. This apparatus includes a first outer wall having an anterior end, a posterior end, an inner surface and an outer surface, the inner surface defining an interior portion, the interior portion having an anterior end and a posterior end, and a light source disposed within the interior portion. The first outer wall has an opening in the posterior end, the opening having an opening diameter. The interior portion has a substantially frusto-conical shape and has a cross-sectional diameter at the opening equal to the opening diameter and a second cross-sectional diameter near the anterior end that is less than the opening diameter and the inner surface is photo-reflective. The light passes through a sample through an aperture and a collector lens or a second outer wall. A transmission diffraction grating may be utilized.

22 Claims, 8 Drawing Sheets

(56) References Cited

U.S. PATENT DOCUMENTS

| | | |
|---|---|---|
| 5,028,787 A | 7/1991 | Rosenthal et al. |
| 5,077,476 A | 12/1991 | Rosenthal |
| 5,086,229 A | 2/1992 | Rosenthal et al. |
| 5,112,124 A | 5/1992 | Harjunmaa et al. |
| 5,137,023 A | 8/1992 | Mendelson et al. |
| 5,183,042 A | 2/1993 | Harjunmaa et al. |
| 5,222,496 A | 6/1993 | Clarke et al. |
| 5,255,171 A | 10/1993 | Clark |
| 5,423,983 A | 6/1995 | Chiang et al. |
| 5,522,388 A | 6/1996 | Ishikawa et al. |
| 5,529,065 A | 6/1996 | Tsuchiya |
| 5,535,743 A | 7/1996 | Backhaus et al. |
| 5,553,613 A | 9/1996 | Parker |
| 5,576,544 A | 11/1996 | Rosenthal |
| 5,615,672 A | 4/1997 | Braig et al. |
| 5,615,673 A | 4/1997 | Berger et al. |
| 5,666,956 A | 9/1997 | Buchert |
| 5,671,301 A | 9/1997 | Kupershmidt |
| 5,703,364 A | 12/1997 | Rosenthal |
| 5,743,262 A | 4/1998 | Lepper, Jr. et al. |
| 5,910,109 A | 6/1999 | Peters et al. |
| 6,025,597 A | 2/2000 | Sterling et al. |
| 6,043,492 A | 3/2000 | Lee et al. |
| 6,064,898 A | 5/2000 | Aldrich |
| 6,067,463 A | 5/2000 | Jeng et al. |
| 6,097,975 A | 8/2000 | Petrovsky et al. |
| 6,134,458 A | 10/2000 | Rosenthal |
| 6,151,517 A | 11/2000 | Honigs et al. |
| 6,181,958 B1 | 1/2001 | Steuer et al. |
| 6,205,354 B1 | 3/2001 | Gellermann et al. |
| 6,208,788 B1 | 3/2001 | Nosov |
| 6,304,767 B1 | 10/2001 | Soller et al. |
| 6,312,393 B1 | 11/2001 | Abreu |
| 6,337,564 B2 | 1/2002 | Manzini et al. |
| 6,403,944 B1 | 6/2002 | MacKenzie et al. |
| 6,421,548 B1 | 7/2002 | Berman et al. |
| 6,424,848 B1 | 7/2002 | Berman et al. |
| 6,424,849 B1 | 7/2002 | Berman et al. |
| 6,424,851 B1 | 7/2002 | Berman et al. |
| 6,430,424 B1 | 8/2002 | Berman et al. |
| 6,445,938 B1 | 9/2002 | Berman et al. |
| 6,522,903 B1 | 2/2003 | Berman et al. |
| 6,574,490 B2 | 6/2003 | Abbink et al. |
| 6,671,528 B2 | 12/2003 | Steuer et al. |
| 6,684,099 B2 | 1/2004 | Ridder et al. |
| 6,723,048 B2 | 4/2004 | Fuller |
| 6,731,963 B2 | 5/2004 | Finarov et al. |
| 6,775,564 B1 | 8/2004 | Peters et al. |
| 6,804,002 B2 | 10/2004 | Fikhte et al. |
| 6,833,540 B2 | 12/2004 | MacKenzie et al. |
| 6,865,408 B1 | 3/2005 | Abbink et al. |
| 6,873,865 B2 | 3/2005 | Steuer et al. |
| 6,958,039 B2 | 10/2005 | Burd et al. |
| 6,968,222 B2 | 11/2005 | Burd et al. |
| 6,990,365 B1 | 1/2006 | Parker et al. |
| 6,993,372 B2 | 1/2006 | Fine et al. |
| 7,039,447 B2 | 5/2006 | Berman et al. |
| 7,043,289 B2 | 5/2006 | Fine et al. |
| 7,107,087 B2 | 9/2006 | Hwang et al. |
| 7,133,711 B2 | 11/2006 | Chernoguz et al. |
| 7,254,432 B2 | 8/2007 | Fine |
| 7,266,400 B2 | 9/2007 | Fine et al. |
| 7,409,239 B2 | 8/2008 | Chung et al. |
| 7,424,317 B2 | 9/2008 | Parker et al. |
| 7,809,418 B2 | 10/2010 | Xu |
| 7,961,305 B2 | 6/2011 | Xu et al. |
| 8,272,771 B2 * | 9/2012 | Arai ............... 362/608 |
| 8,340,738 B2 | 12/2012 | Xu |
| 2001/0030742 A1 | 10/2001 | Kramer et al. |
| 2001/0039376 A1 | 11/2001 | Steuer et al. |
| 2002/0010563 A1 | 1/2002 | Ratteree et al. |
| 2002/0016534 A1 | 2/2002 | Trepagnier et al. |
| 2002/0019055 A1 | 2/2002 | Brown et al. |
| 2002/0161289 A1 | 10/2002 | Hopkins et al. |
| 2002/0167704 A1 | 11/2002 | Kleinhans et al. |
| 2003/0004423 A1 | 1/2003 | Lavie et al. |
| 2003/0023152 A1 | 1/2003 | Abbink et al. |
| 2003/0078504 A1 | 4/2003 | Rowe |
| 2004/0015734 A1 | 1/2004 | Rahman |
| 2004/0087844 A1 | 5/2004 | Yen |
| 2004/0106163 A1 | 6/2004 | Workman et al. |
| 2004/0127779 A1 | 7/2004 | Steuer et al. |
| 2004/0181132 A1 | 9/2004 | Rosenthal |
| 2004/0225205 A1 | 11/2004 | Fine et al. |
| 2004/0225206 A1 | 11/2004 | Kouchnir |
| 2005/0131286 A1 | 6/2005 | Parker et al. |
| 2005/0261560 A1 * | 11/2005 | Ridder et al. ............... 600/310 |
| 2005/0272987 A1 | 12/2005 | Kiani-Azarbayjany et al. |
| 2005/0276072 A1 * | 12/2005 | Hayashi et al. ............... 362/609 |
| 2006/0009685 A1 | 1/2006 | Finarov et al. |
| 2006/0058622 A1 | 3/2006 | Tearney et al. |
| 2006/0063983 A1 | 3/2006 | Yamakoshi |
| 2006/0129040 A1 | 6/2006 | Fine et al. |
| 2006/0152726 A1 | 7/2006 | Larsen et al. |
| 2006/0200014 A1 | 9/2006 | Fine et al. |
| 2006/0224057 A1 | 10/2006 | Burd et al. |
| 2006/0226992 A1 | 10/2006 | Al-Ali et al. |
| 2006/0250676 A1 | 11/2006 | Hagood |
| 2006/0258918 A1 | 11/2006 | Burd et al. |
| 2006/0264719 A1 | 11/2006 | Schurman et al. |
| 2007/0049811 A1 | 3/2007 | Kobayashi et al. |
| 2007/0078312 A1 | 4/2007 | Fine et al. |
| 2007/0149869 A1 | 6/2007 | Yen |
| 2008/0027297 A1 | 1/2008 | Yamakoshi |
| 2008/0144004 A1 | 6/2008 | Rosenthal |
| 2008/0194014 A1 | 8/2008 | Young et al. |
| 2008/0266900 A1 * | 10/2008 | Harbers et al. ............... 362/609 |
| 2009/0059586 A1 | 3/2009 | Livesay et al. |
| 2009/0079964 A1 | 3/2009 | Xu |
| 2009/0105565 A1 | 4/2009 | Xu |
| 2009/0116017 A1 | 5/2009 | Xu et al. |
| 2009/0247843 A1 | 10/2009 | Xu |
| 2009/0270700 A1 | 10/2009 | Van Herpen et al. |
| 2009/0292186 A1 | 11/2009 | Xu |
| 2010/0026995 A1 | 2/2010 | Merritt et al. |
| 2013/0006070 A1 | 1/2013 | Xu |
| 2013/0006071 A1 | 1/2013 | Xu |
| 2013/0006072 A1 | 1/2013 | Xu |
| 2013/0006073 A1 | 1/2013 | Xu |

FOREIGN PATENT DOCUMENTS

| | | |
|---|---|---|
| CN | 1932840 | 3/2007 |
| EP | 01094745 A1 | 5/2001 |
| EP | 1281370 A2 | 2/2003 |
| JP | 720551 U | 4/1995 |
| JP | 9010238 | 1/1997 |
| JP | 11037931 A | 2/1999 |
| JP | 2004267613 A | 9/2004 |
| JP | 2004290544 A | 10/2004 |
| SU | 1193541 A1 | 11/1985 |
| WO | 90/13092 A1 | 11/1990 |
| WO | 9115991 A1 | 10/1991 |
| WO | 9115992 A1 | 10/1991 |
| WO | 9300856 A1 | 1/1993 |
| WO | 93/06774 A1 | 4/1993 |
| WO | 9413199 A1 | 6/1994 |
| WO | 9416614 A1 | 8/1994 |
| WO | 9531930 A1 | 11/1995 |
| WO | 9604840 A1 | 2/1996 |
| WO | 9617546 A1 | 6/1996 |
| WO | 96/39926 | 12/1996 |
| WO | 9639927 A1 | 12/1996 |
| WO | 9803847 A2 | 1/1998 |
| WO | 9836681 A1 | 8/1998 |
| WO | 99/16136 A1 | 4/1999 |
| WO | 9939631 A1 | 8/1999 |
| WO | 0001294 A1 | 1/2000 |
| WO | 0016688 A1 | 3/2000 |
| WO | 01/16578 A1 | 3/2001 |
| WO | 0193755 A1 | 12/2001 |
| WO | 0196872 A2 | 12/2001 |
| WO | 02082990 A1 | 10/2002 |
| WO | 03010510 A2 | 2/2003 |
| WO | 03/077756 A1 | 9/2003 |

| | | | |
|---|---|---|---|
| WO | 2005045377 A2 | 5/2005 |
| WO | 2006086566 A2 | 8/2006 |
| WO | 2006094109 A1 | 9/2006 |
| WO | 2007122557 A2 | 11/2007 |
| WO | 2008/039195 A1 | 4/2008 |
| WO | 2009/035669 A1 | 3/2009 |
| WO | 2009/045492 A1 | 4/2009 |
| WO | 2009/120600 A2 | 10/2009 |
| WO | 2009/142853 A1 | 11/2009 |
| WO | 2010017238 A1 | 2/2010 |
| WO | 2010114736 | 10/2010 |

OTHER PUBLICATIONS

International Preliminary Report on Patentability (Chapter II) for PCT/US2009/040942 dated Dec. 13, 2010.
International Preliminary Report on Patentability (Chapter II) for PCT/US2009/037805 dated Dec. 14, 2010.
International Preliminary Report on Patentability (Chapter II) for PCT/US2008/011438 dated Jun. 18, 2010.
International Search Report and Written Opinion for PCT/US2010/028255 dated May 19, 2010.
International Search Report for PCT/US2008/010670 dated Nov. 21, 2008.
International Search Report for PCT/US2008/011438 dated Dec. 9, 2008.
Office Action for U.S. Appl. No. 12/256,028 dated May 24, 2010.
Office Action for U.S. Appl. No. 12/209,807 dated May 17, 2010.
Wagner et al., "Invasiveness as a Barrier to Self-Monitoring of Blood Glucose in Diabetes", Diabetes Technology & Therapeutics, Aug. 1, 2005.
Web Page Document entitled http://www.orsense.com/Diabetes_ Monitoring dated Aug. 9, 2007.
Office Action for U.S. Appl. No. 12/209,807 dated Sep. 17, 2010.
Office Action for U.S. Appl. No. 12/256,028 dated Sep. 15, 2010.
Office Action for U.S. Appl. No. 12/425,535 dated May 16, 2012.
Office Action for RU Application 2010117396 dated Jun. 18, 2012.
Office Action for CN Application 200980126116.7 dated Jun. 4, 2012.
Office Action for RU Application 2010114587 dated Jun. 22, 2012.
Office Action for U.S. Appl. No. 12/407,999 dated Nov. 21, 2012.
Office Action for CN Application 200880114960.3 dated Jan. 29, 2013.
Office Action for JP Application 2010-524873 dated Dec. 25, 2012.
Office Action for JP Application 2010-527994 dated Dec. 25, 2012.
Office Action for CN Application 200980126116.7 dated Feb. 16, 2013.
Office Action for U.S. Appl. No. 12/425,535 dated Mar. 22, 2012.
Extended European Search Report for EP Application 08830786.3 dated Apr. 22, 2013.
Office Action for RU Application 2010152373 dated Mar. 26, 2013.

* cited by examiner

OPTICAL SPECTROSCOPY DEVICE FOR NON-INVASIVE BLOOD GLUCOSE DETECTION AND ASSOCIATED METHOD OF USE

CROSS-REFERENCE TO RELATED APPLICATION

This patent application claims priority to U.S. Provisional Patent Application Ser. No. 61/165,547 filed Apr. 1, 2009, the disclosure of which is incorporated herein by reference.

BACKGROUND OF THE INVENTION

Diabetes is a chronic disease that, when not controlled, over time leads to serious damage to many of the body's systems, including the nerves, blood vessels, eyes, kidneys and heart. The National Institute of Diabetes and Digestive and Kidney Diseases (NIDDK) estimates that 23.6 million people or 7.8 percent of the population in the United States had diabetes in 2007. Globally, the World Health Organization (WHO) estimates that more than 180 million people have diabetes, a number they expect to increase to 366 million by 2030, with 30.3 million in the United States. According to the WHO, an estimated 1.1 million people died from diabetes in 2005. They project that diabetes deaths will increase by more than 50% between 2006 and 2015 overall and by more than 80% in upper-middle income countries.

The economic burden from diabetes for individuals and society as a whole is substantial. According to the American Diabetes Association, the total annual economic cost of diabetes was estimated to be $174 billion in the United States in 2007. This is an increase of $42 billion since 2002. This 32% increase means the dollar amount has risen over $8 billion more each year.

A vital element of diabetes management is the self-monitoring of blood glucose (SMBG) concentration by diabetics in the home environment. By testing blood glucose levels often, diabetics can better manage medication, diet, and exercise to maintain control and prevent the long-term negative health outcomes. In fact, the Diabetes Control and Complications Trial (DCCT), which followed 1,441 diabetics for several years, showed that those following an intensive-control program with multiple blood sugar tests each day as compared with the standard-treatment group had only one-fourth as many people develop diabetic eye disease, half as many develop kidney disease, one-third many develop nerve disease, and far fewer people who already had early forms of these three complications got worse.

However, current monitoring techniques discourage regular use due to the inconvenient and painful nature of drawing blood through the skin prior to analysis, which causes many diabetics to not be as diligent as they should be for good blood glucose control. As a result, non-invasive measurement of glucose concentration is a desirable and beneficial development for the management of diabetes. A non-invasive monitor will make testing multiple times each day pain-free and more palatable for children with diabetes. According to a study published in 2005 (J, Wagner, C. Malchoff, and G. Abbott, Diabetes Technology & Therapeutics, 7(4) 2005, 612-619), people with diabetes would perform SMBG more frequently and have improved quality of life with a non-invasive blood glucose monitoring device.

There exist a number of non-invasive approaches for blood glucose determination. One technique of non-invasive blood chemicals detection involves collecting and analyzing light spectra data.

Extracting information about blood characteristics such as glucose concentration from spectral or other data obtained from spectroscopy is a complex problem due to the presence of components (e.g., skin, fat, muscle, bone, interstitial fluid) other than blood in the area that is being sensed. Such other components can influence these signals in such a way as to alter the reading. In particular, the resulting signal may be much larger in magnitude than the portion of the signal that corresponds to blood, and therefore limits the ability to accurately extract blood characteristics information.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION OF THE INVENTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, and logical changes may be made without departing from the scope of the present invention. The following detailed description is, therefore, not to be taken in a limiting sense, and the scope of the present invention is defined by the appended claims and their equivalents.

In this document, the terms "a" or "an" are used to include one or more than one and the term "or" is used to refer to a nonexclusive "or" unless otherwise indicated. In addition, it is to be understood that the phraseology or terminology employed herein, and not otherwise defined, is for the purpose of description only and not of limitation. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

Embodiments of the present invention relate to optical components, such as light funnels for illumination and measurement of optical properties of a sample. Although spectroscopic sampling of human or animal body regions are exemplified, the embodiments relate to all types of optical instrumentation, including optical detectors, microscopes, spectrometers, etc.

Optical spectroscopy can be used to determine the amount of light absorbed by a biological sample such as human finger. By measuring the amount of light absorbed by the finger, it is possible to determine glucose, cholesterol, and hemoglobin levels of a person non-invasively. Fingertip measurements are usually preferred because of the large concentration of capillaries in the fingertip and because of the conversion of arterial blood into venous blood that occurs in the fingertip. However, the techniques of the present invention are not limited to use with a human finger. For example, the use of other samples, such as a human earlobe, may be desirable.

Figure 1:
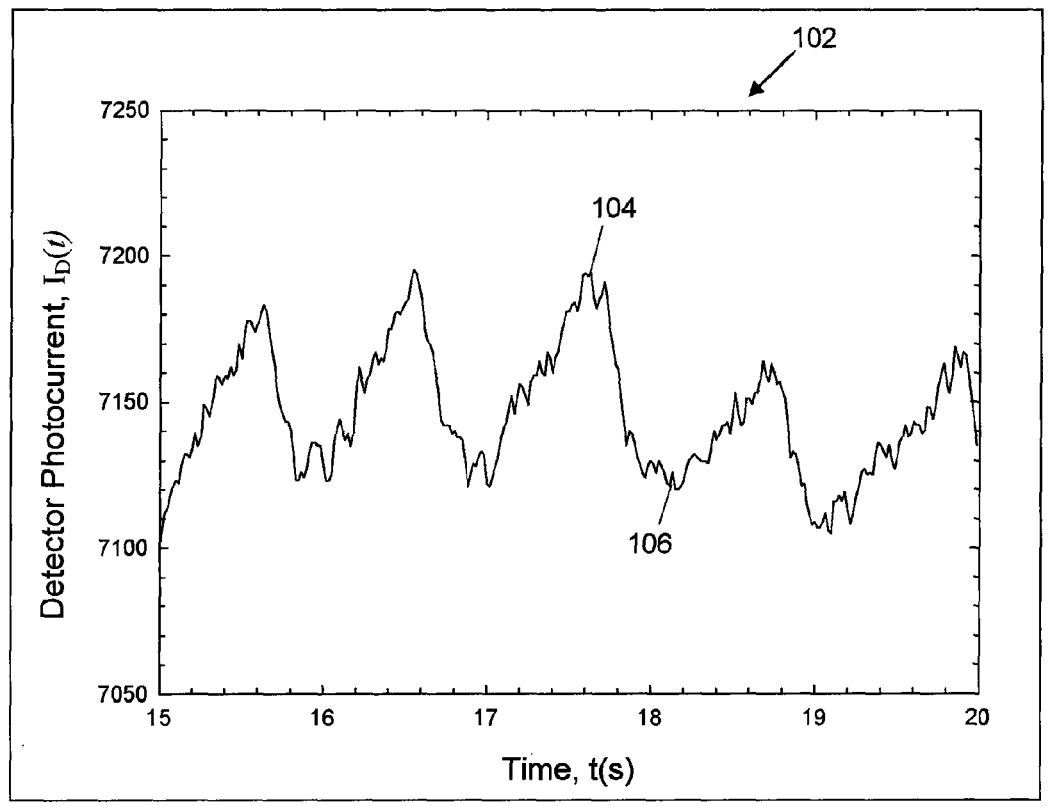
FIG. 1 illustrates a plot of a pulse wave corresponding to light absorption of arterial blood, according to some embodiments.

When light is transmitted through a biological sample, such as a human finger, the light is absorbed and scattered by various components of the finger including skin, muscle, bone, fat, interstitial fluid and blood. It has been observed, however, that light absorption by a human finger exhibits a small cyclic pattern that corresponds to a heartbeat. FIG. 1 depicts a plot 102 of a cyclic detector photocurrent, $I_D(t)$, that corresponds to the light absorption of arterial blood in the capillary due to the heartbeat of the user. Although the magnitude of the cyclic pattern is small in comparison to the total photocurrent generated by the detector, considerable information can be extracted from the cyclic pattern of the plot 102. For example, assuming that the person's heart rate is sixty beats per minute, the time between the start of any pulse beat and the end of that pulse beat is one-second. During this one-second period, the photocurrent will have a maximum or peak 104 reading and minimum or valley 106 reading. The peak 104 reading of the plot corresponds to when there is a minimum amount of blood in the capillaries, and the valley 106 reading corresponds to when there is a maximum amount of blood in the capillaries. By using information provided by the peak and valley of the cyclic plot, the optical absorption and scattering by major finger constituents that are not in the capillaries such as skin, fat, bones, muscle, and interstitial fluids are excluded. These major constituents that are not in the capillaries are excluded because they are not likely to change during the time interval of one heartbeat. In other words, the light that is absorbed by the blood can be detected based on the peaks and valleys of the plot 102.

Assuming that the peak of the cyclic photocurrent generated by the light-sensing device is $I_P$, the adjacent valley of the cyclic photocurrent is $I_V$, and the photocurrent generated by the light-sensing device without a sample is $I_0$, the transmittances corresponding to the peak and valley photocurrents can be defined as:

$$T_V = \frac{I_V}{I_0}; \tag{1}$$

and $$T_P = \frac{I_P}{I_0}; \tag{2}$$

The corresponding peak and valley absorbance are:

$$A_V = -\log(T_V) \tag{3}$$

and $$A_P = -\log(T_P) \tag{4}$$

The difference between $A_V$ and $A_P$ reflects the light absorption and scattering by only the blood in the finger:

$$\Delta A = A_V - A_P = \log\left(\frac{I_P}{I_V}\right); \tag{5}$$

The algorithm shown in equation (5) only requires monitoring the photocurrent corresponding to light power transmitted through the finger. As a result, there is no need to determine photocurrent generated by the light-sensing device without a human finger.

Figure 2:
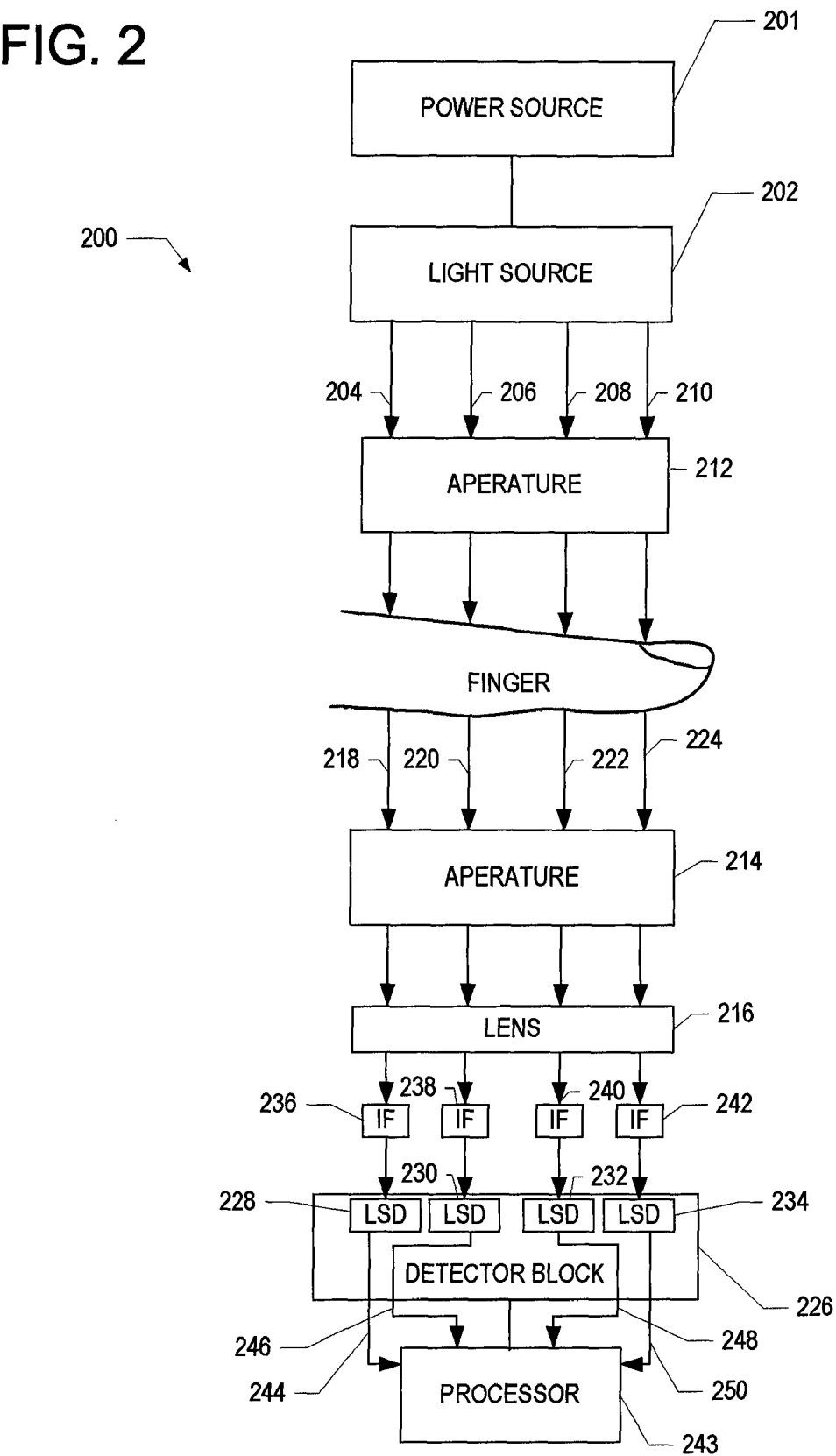
FIG. 2 is a simplified block diagram that illustrates the components of an optical measurement system according to the present invention.

FIG. 2 is a simplified block diagram that illustrates components of a current optical measurement system, which is generally indicated by numeral 200, which uses the "pulsatile" concept for determining an amount of light absorbed and scattered solely by the blood in a sample (e.g. human finger). A power source 201, such as a battery, provides power to a light source 202 that generates a plurality of light beams 204, 206, 208, 210 that are directed toward the top of the finger of a user. According to one aspect of the optical measurement system 200, each of the light beams 204, 206, 208, 210 have the same wavelength range, typically from about 700 nm to about 1600 nm. Although the optical measurement system 200 is described herein as generating four (4) light beams, it is contemplated that the light source 202 can be altered to generate fewer light beams or additional light beams in other embodiments.

A first aperture 212 ensures that the light beams 204, 206, 208, 210 strike a target area of the sample (e.g. human finger). A second aperture 214 ensures that the portion of the light beams that are transmitted through the sample strike a lens 216. Light beams 204, 206, 208, 210 are attenuated by the sample and components of the optical measurement system 200, and, thus, attenuated light beams 218, 220, 222, 224 are emitted from the sample. The attenuated light beams 218, 220, 222, 224 strike the lens 216, and the lens 216 collects the attenuated light beams 218, 220, 222, 224 so that they impinge more efficiently on a detector block 226.

The detector block 226 is positioned directly under the lens 216 and comprises a plurality of light-sensing devices (LSD) 228, 230, 232, 234 such as an array of photodiodes. According to one aspect of the optical measurement system 200, each of the light-sensing devices 228, 230, 232, 234 is tuned to detect a specific spectrum (or spectrums) of light. For example, each light-sensing device may be associated with a corresponding interference filter (IF), such as filters 236, 238, 240, 242. An interference filter transmits one or more spectral bands or lines of light, and substantially blocks others.

Each of the light-sensing devices 228, 230, 232, 234 generates a corresponding photocurrent signal 244, 246, 248, 250 that is proportional to the power of the light received by the particular light sensing device. The photocurrent signal generated by the photodiode can be converted to another form of signal, such as an analog voltage signal or a digital signal.

Processor 243 is coupled to the detector block 226 and is configured to calculate the change of photocurrent signals 244, 246, 248, 250. In an exemplary embodiment, processor 243 executes an algorithm such as shown in the Equation indicated by numeral (5) above, to calculate the change in the light absorption (ΔA) solely caused by the blood in the finger. Thereafter, this quantitative calculation of light absorption of the blood can be used to determine a characteristic of the blood. For example, by comparing the calculated light absorption value to predetermined values corresponding to different glucose levels stored in a memory (not shown), a glucose level of the user can be determined.

A difficulty associated with the finger based pulsatile detection methodology is low signal-to-noise ("S/N") ratio, because the amplitude of cyclic pattern (i.e., the difference between peak and valley) is typically 1%-2% of the total photocurrent generated by the light power transmitted through the sample (e.g. a person's finger). To obtain a S/N ratio of 100:1 in the determination of ΔA, the baseline noise of the device being used to measure the light absorption by the sample should not be larger than $3.0 \times 10^{-5}$ in absorbance (peak to peak), within a 10 Hz bandwidth.

However, a $3.0 \times 10^{-5}$ absorbance (peak to peak) baseline noise level within a 10 Hz bandwidth is difficult to obtain with the low light power levels that are used by some battery-powered hand held non-invasive blood chemicals measurement devices.

One known solution involves data averaging. To increase the S/N ratio, the averaged value of ΔA, as defined by the equation below, is used in further calculation to extract blood glucose concentration:

$$\overline{\Delta A} = \sum_{j=1}^{M} \Delta A_j$$

In this equation, M is the number of heartbeats during the time interval of the pulsatile measurement. However, this approach requires long data acquisition time, due to the fact that the rate of heartbeat is in the order of one per second. For example, 25 seconds would be needed for increasing the S/N ratio by a factor of five, and 100 seconds would be needed for increasing the S/N ratio by a factor of 10. In comparison, current commercial blood drawing glucose meters can determine blood glucose level within 5 seconds. Furthermore, long detection time will significantly increase measurement errors due to finger movement, light power drift, temperature change, etc.

Another solution involves increasing light illumination power. However, due to size limitations of some devices, it may not be possible or it may be inefficient to increase illumination power to achieve a desired baseline noise level (e.g., battery drain). Thus, there is a need for a system and method to increase the amount of light power that can be detected by such devices without significantly increasing device size, light illumination power, and battery power consumption.

Figure 3:
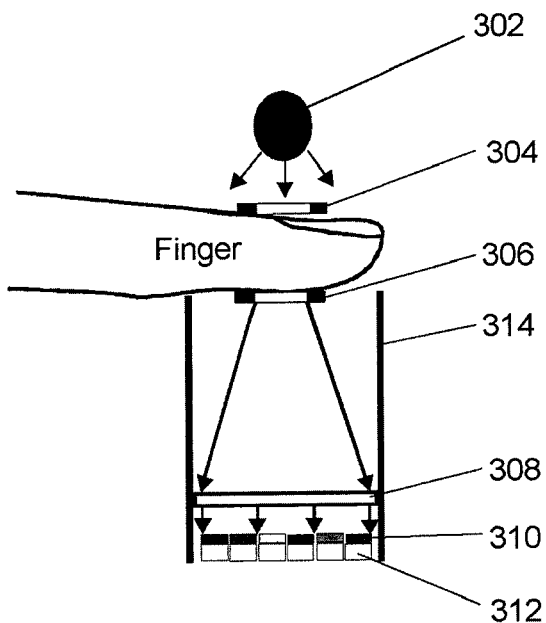
FIG. 3 illustrates an existing optical configuration for performing optical measurements of a biological sample, according to some embodiments.

FIG. 3 depicts the configuration of a conventional, prior art apparatus for measuring the amount of light absorbed by a sample (e.g. human finger). A lamp 302 generates near infrared ("NIR") radiation or light beams from 700 nm to 1600 nm. The generated NIR light beams enter an entrance aperture 304 and pass through the sample. The NIR light beams transmitted through the sample pass through an exit aperture 306 onto a lens 308. The lens 308 collimates light beams and projects them onto filter array 310 and then detector array 312. The apparatus also includes a wall housing 314 to prevent stray light from reaching the light detectors.

The optical system shown in FIG. 3 has very low optical power efficiency. Light enters the sample via entrance aperture 304. Typically, to accommodate small finger size of children, entrance aperture 304 has a diameter of approximately 0.25 (¼) inches or less. Light transmitted through the sample is collected through an exit aperture 306. Exit aperture 306 typically has a diameter of approximately 0.25 (¼) inches or less. Most light power emitted from the lamp 302 cannot reach the target area due to a small illumination solid angle. The optical configuration shown in FIG. 3 also has a small solid angle for light collection. Light is emitted from the exit aperture 306 into the entire 2π solid angle beneath the sample. The total light power collected using optical system shown in FIG. 3 is typically about 10% of the light power emitted through the aperture 306. Furthermore, the entire light power distribution from 700 nm to 1600 nm is transmitted to every detector in the detector array 312, and each detector typically detects only a relatively narrow wavelength bandwidth, ~10 nm. As such, up to 98% of light power (or more) is wasted.

Figure 4A:
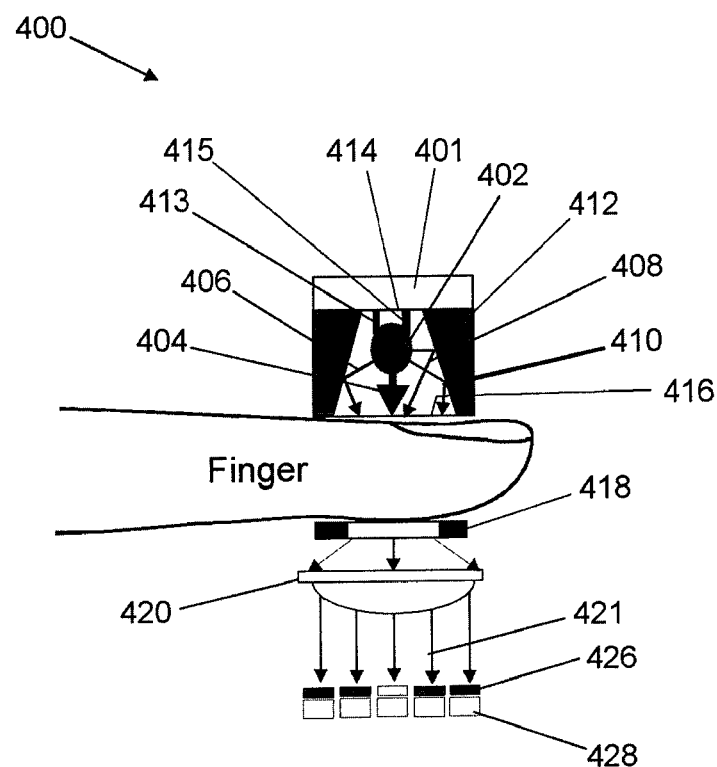
FIG. 4A illustrates a first alternative embodiment for performing optical measurements of a biological sample.

FIG. 4A depicts an optical measurement system 400 for performing optical detection of a biological sample according to an exemplary, first alternative embodiment. The system includes light illumination funnel 412, which may be constructed according to the techniques described below with reference to FIG. 5. A small light source 402, e.g., lamp, is disposed within the interior portion of light illumination funnel 412, and generates a plurality of light beams 404, 406, 408, 410. Each of the light beams 404, 406, 408, 410 have the same wavelength range from about 700 nm to about 1600 nm, for example. Although the optical measurement system 400 is described herein as generating four (4) light beams, it is contemplated that the light source can be altered to generate fewer light beams or additional light beams in other embodiments.

The light beams 404, 406, 408, 410 from the light source 402 exit the light illumination funnel 412 through an exit opening 416, with some of the beams being reflected by the sidewall of the funnel. The diameter of the exit opening 416 of the light illumination funnel 412 is larger than or equal to the funnel diameter 414 near the anterior end. Electrodes 413 and 415 of the light source 402 are connected to the lamp control board 401. For example, according to one embodiment the funnel diameter 414 is approximately 0.125 (⅛) inch and the diameter of the exit opening 416 is approximately 0.25 (¼) inch. Accordingly, in contrast to the configuration depicted in FIG. 3, the light illumination funnel 412 focuses the light beams 404, 406, 408, 410 into the same general direction toward the top of the sample. The light illumination funnel may significantly increase the total light power received by the target area in comparison to the configuration of FIG. 3, and therefore substantially increase the S/N ratio.

Figure 4B:
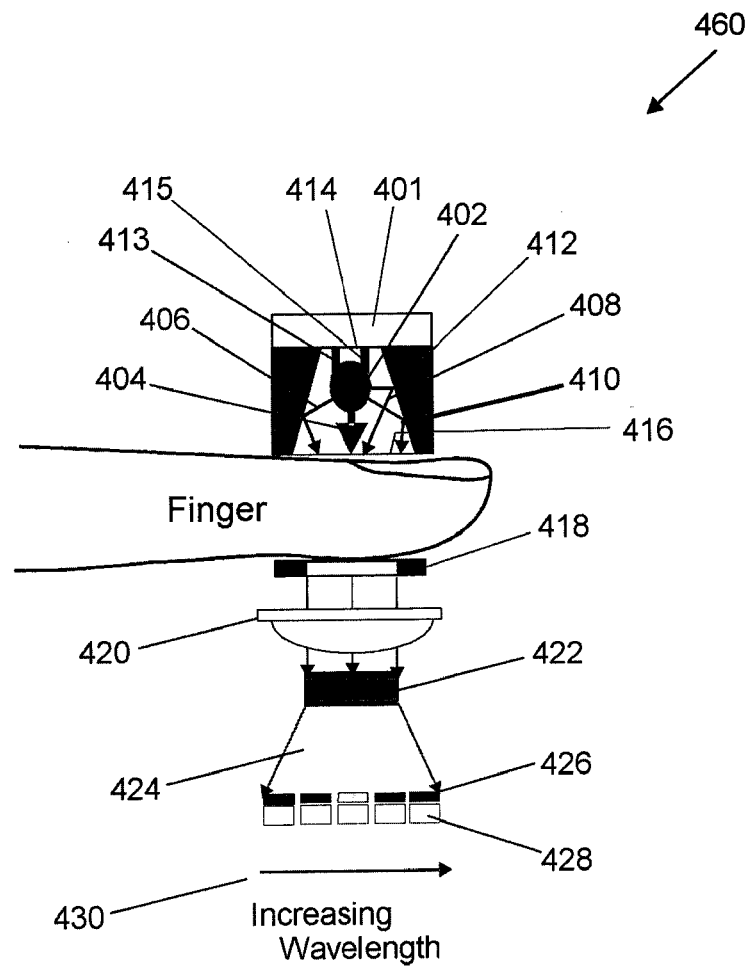
FIG. 4B illustrates a preferred embodiment for performing optical measurements of a biological sample.
Figure 4C:
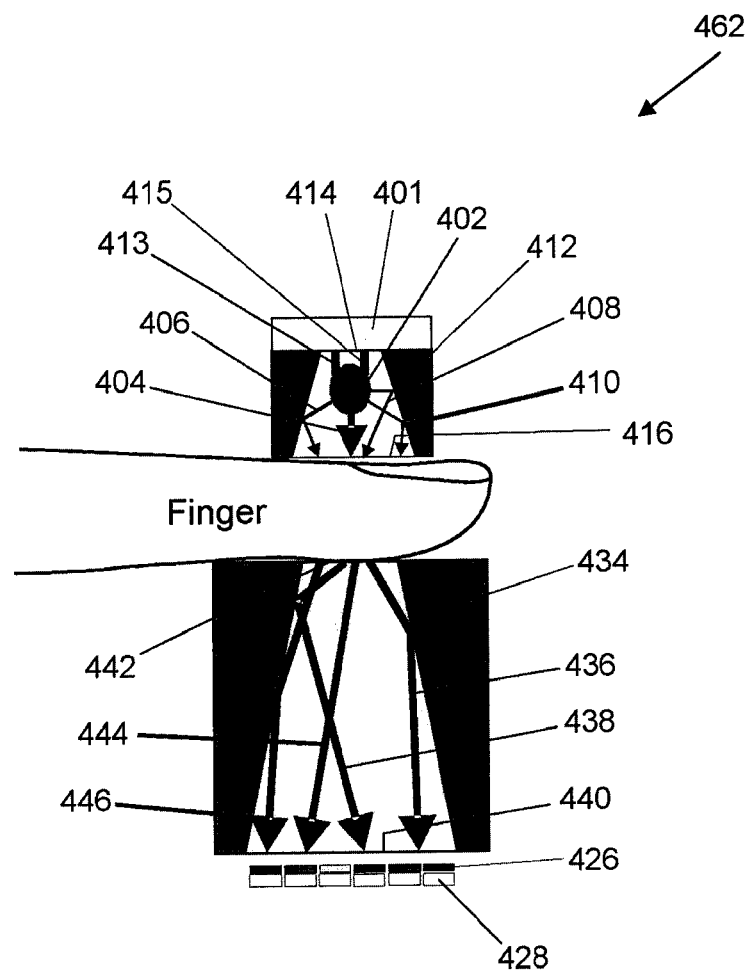
FIG. 4C illustrates a second alternative embodiment for performing optical measurements of a biological sample.
Figure 5:
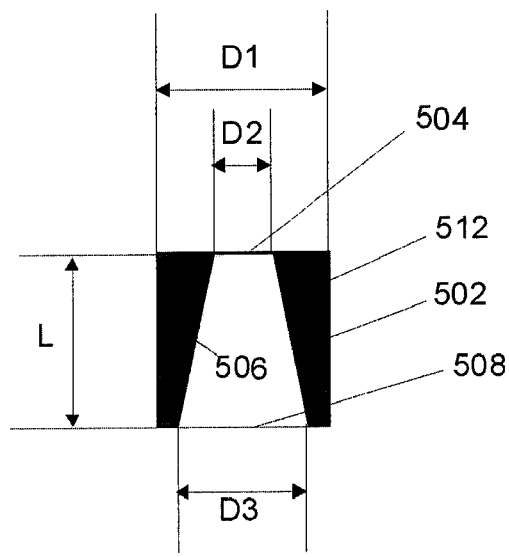
FIG. 5 is a cross-sectional view of an exemplary light funnel and half angle ($\alpha$)
Figure 5:
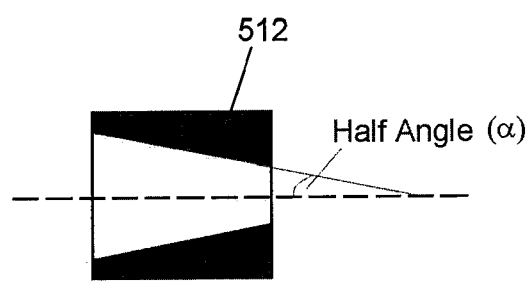

FIG. 5 depicts a cross sectional view of an exemplary light funnel 512. Light funnel 512 could be used as a light illumination funnel e.g., 412 in FIG. 4A, 4B, or 4C, or light collection funnel, e.g. 434 in FIG. 4C. Exemplary light funnel 512 has a substantially cylindrical outer wall 502 with diameter D1, and an interior portion defined by an inner wall 506 that has a substantially frusto-conical shape. The interior portion of the funnel has a diameter D2 at the anterior end 504. The funnel has an exit opening 508 at the posterior end. Opening 508 (light exit) has a diameter D3 that is larger than D2. The separation distance between the two ends is L, and the Half Angle of the frusto-conical shape of the inner surface is α. The Half Angles may be less than about 45 degrees, for example. In an exemplary embodiment, the value of Half Angle α is about 5 to about 25 degrees. The light funnel 512 may be formed from plastic, metal, or other suitable material or compound/layers of material, with any desired refractive index(es). According to one aspect, the light funnel 512 is formed from metal and the surface of inner wall 506 is made highly reflective. With the light illumination funnel, the total light illumination power received by the target area may be increased by a factor of 3 to 4 over the light illumination configuration shown in FIG. 3.

Figure 6:
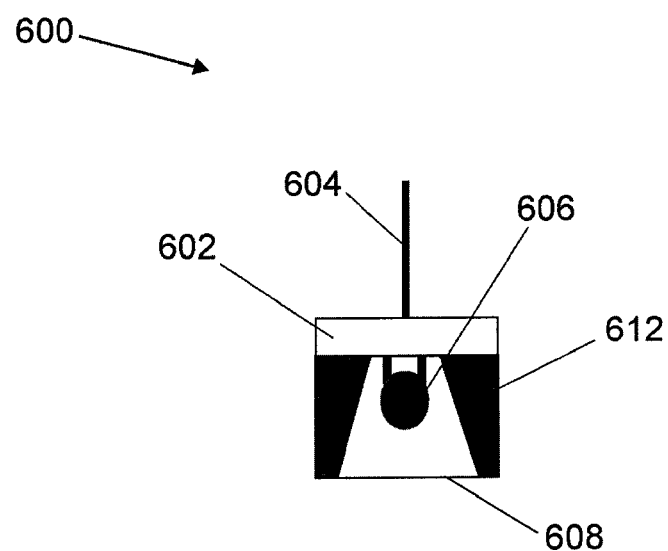
FIG. 6 is a cross-sectional view of an exemplary light funnel and light source.

FIG. 6 depicts an exemplary optical apparatus, which is generally indicated by numeral 600, which includes a light source 606, e.g., lamp, and a light illumination funnel 612. A printed circuit board ('PCB') 602 for lamp power control may be positioned near or in contact with the anterior end of the light illumination funnel. Light source 606, e.g., lamp, is connected to the board 602 via wires that pass through the anterior end of the funnel. Light source 606, e.g., lamp, may be mounted to the PCB 602. The PCB 602 receives electric power through power lines 604 that is connected to a power source, e.g., power source 201, e.g., battery, shown in FIG. 2. When the electric power is supplied through the power lines 604, the light source 606, e.g., lamp, generates a plurality of light beams e.g., light beams 404, 406, 408, and 410, shown in FIGS. 4A, 4B, and 4C. The position of the light source 606, e.g., lamp, inside the funnel can be adjusted as to maximize the illumination power received by the large opening 608 (the light exit).

In an exemplary embodiment, light illumination funnel 612 is mounted to PCB 602 via screws, posts or other connecting means. The frusto-conical shape of the inner surface of the light illumination funnel 612 serves to concentrate and focus the light beams 404, 406, 408, 410, shown in FIGS. 4A, 4B, and 4C, from the lamp into a generally conical beam toward the finger.

Referring again to FIG. 4A, light beams 404, 406, 408, 410 are attenuated by the sample and components of the optical measurement system 400. The attenuated light beams then pass an exit aperture 418, collected by a condenser lens 420, e.g., aspheric lens. The beams 421 exiting the condenser lens 420, e.g., aspheric lens, may then pass through filters 426 to detectors 428.

An advantage of using a condenser lens 420, e.g., aspheric lens, for light collection is its large solid angle for light collection. When configured properly, the total light power received by each detector may be increased by a factor 3 to 4 when a condenser lens 420, e.g., aspheric lens, is used for collecting light emitted from the target area in comparison to the light collection configuration shown in FIG. 3. The combination of utilizing a light illumination funnel 412 and an condenser lens 420, e.g., aspheric lens, as light collector may increase the total light power received by each detector by about nine times to about sixteen times in comparison to the optical configuration shown in FIG. 3.

The detector block 428 is positioned beneath the condenser lens 420, e.g., aspheric lens, and may include a plurality of light-sensing devices, such as an array of photodiodes. Each of the light-sensing devices detects a specific spectrum of light. In an exemplary embodiment, an interference filter 426 is placed on top of each light-sensing device.

A processor, e.g., processor 243 shown in FIG. 2, may be coupled to the detector block 428 and configured to calculate a change of current signals generated by the light sensing devices. For example, as described above in reference to FIG. 2, the processor 243 executes an algorithm such as shown in equation (5) to calculate the change in the light absorption (AA) solely caused by the blood in a finger. Thereafter, this quantitative calculation of light absorption of the blood can be used to determine a characteristic of the blood.

FIG. 4B illustrates a preferred embodiment of optical configuration for performing optical detection of a biological sample and is generally indicated by numeral 460. Light source 402 generates a plurality of light beams 404, 406, 408, 410. The light source 402 may be incandescent light sources or infrared emitting diodes, for example. According to one aspect of the optical measurement system 460, each of the light beams 404, 406, 408, 410 have the same wavelength range from 700 nm to 1600 nm, for example. Although the optical measurement system 460 is described herein as generating four (4) light beams, it is contemplated that the light source can be altered to generate fewer light beams or additional light beams in other embodiments. The light beams 404, 406, 408, 410 from the light source 402 exit the light illumination funnel 412 through an exit opening 416. The diameter of the exit opening 416 of the light illumination funnel 412 is larger than or equal to the diameter of the opening 414 on the top, through which the two electrodes 413 and 415 of the light source 402 is connected to the lamp control board 401. For example, according to one embodiment the diameter of the entrance opening 414 is approximately 0.125 (⅛) inch and the diameter of the exit opening 416 is approximately 0.25 (¼) inch. Accordingly, in contrast to the configuration depicted in FIG. 3, the light illumination funnel 412 focuses the light beams 404, 406, 408, 410 in the same general direction toward the top of the finger of a user. The light illumination funnel may significantly increase the total light power received by the target area in comparison to the configuration of FIG. 3, and therefore substantially increase the S/N ratio.

In the exemplary, preferred embodiment depicted in FIG. 4B indicated by numeral 460, light beams 404, 406, 408, 410 are attenuated by the sample and components of the optical measurement system. The attenuated light NIR beams then pass an exit aperture 418, are collected by a condenser lens 420, e.g., aspheric lens, and projected onto a transmission grating device 422. Transmission diffraction grating 422 angularly resolves the various wavelength components of the mixed NIR light beams into a spectrum with wavelength increasing monotonically in the direction depicted by arrow 430. In other words, because the diffraction angle depends on wavelength, different wavelength components of the light beams are sent to different directions by the diffraction grating 422. The optical spectrum 424 exiting the transmission diffraction grating 422 may then be narrowed down by optional interference filter array 426. Light is detected by photodetector array 428 (e.g. photodiodes). The detectors in array 428 may be positioned so that detectors tuned to a particular spectrum of light receive light from the transmission diffraction grating 422 within that spectrum. For example, the center wavelength of each interference filter in the filter array 426 may be arranged to increase monotonically to coincide with corresponding wavelength component of the spectrum from the transmission diffraction grating 422. It will be apparent that the use of filters, e.g., filter array 426, is optional, and not necessary.

In comparison to the collection optical structure in FIG. 3 where entire light power distribution from 700 nm to 1600 nm is sent to every detector, the approach utilizing transmission diffraction grating will limit the spectrum sent to each detector to wavelength components near the center wavelength of the detector (and/or corresponding filter). As a result, the amount of light wasted is dramatically reduced, and the light power received by the photodiodes may be increased by a factor of 10 times to 20 times in comparison to the light collection configuration described in reference to FIG. 4A. Therefore, the combination of utilizing a light illumination funnel 412, a condenser lens 420, e.g., aspheric lens, as light collector, and a transmission grating 422 as wavelength separation device may increase the light power received by the photodiodes by about 100 to about 200 times in comparison to the optical configuration shown in FIG. 3.

FIG. 4C illustrates an exemplary, second alternative embodiment generally indicated by numeral 462. Although the optical measurement system 462 is described herein as generating four (4) light beams, it is contemplated that the light source can be altered to generate fewer light beams or additional light beams in other embodiments. The light beams 404, 406, 408, 410 from the light source 402 exit the light illumination funnel 412 through an exit opening 416. The diameter of the exit opening 416 of the light illumination funnel 412 is larger than or equal to the diameter of the opening 414 on the top, through which the two electrodes 413 and 415 of the light source 402 is connected to the lamp control board 401. For example, according to one embodiment the diameter of the entrance opening 414 is approximately 0.125 (⅛) inch and the diameter of the exit opening 416 is approximately 0.25(¼) inch. Light illumination funnel 412 illuminates a sample (e.g. a finger). Light beams 404, 406, 408, 410 are attenuated by the sample and components of the optical measurement system. Attenuated light beams 436, 438, 444, 446 are emitted from the sample. Attenuated light beams 436, 438, 444, 446 enter light collection funnel 434 through an entrance opening 442 (first opening) and exit the light collection funnel 434 through an exit opening 440 (second opening). The diameter of the entrance opening 442 of the light collection funnel 434 is less than or equal to the diameter of the exit opening 440. For example, according to one embodiment, the diameter of the exit opening 440 is approximately 0.625 (⅝) inch and the diameter of the entrance opening 442 is approximately 0.25 (¼) inch. Light collection funnel 434 may project the collected light onto filter array 426.

Light collection funnel 434 may be constructed according to the techniques described below with reference to FIG. 5. For example, exemplary light collection funnel 434 has a substantially cylindrical outer wall 502 and a central opening defined by an inner wall 506 that is of a frusto-conical shape. The light funnel collector 434 may also be formed from plastic, metal, or other suitable material or compound/layers of material with any desired refractive index(es). Light collection funnel 434 may be formed from metal and the surface of the frusto-conical shape inner wall may be made highly reflective. It has been observed that the overall collection efficiency of light collection funnel 434 is over 80%, which is eight times that obtained using traditional optical collection structure shown in FIG. 3. The combination of utilizing a light illumination funnel 412 and light collection funnel 434 may increase the light power received by the detectors by about 20 to about 30 times in comparison to the optical configuration in FIG. 3

Filter array 426 and detector array 428 are positioned beneath the exit opening 440 of the light collection funnel 434 and comprises a plurality of light-sensing devices, e.g. light sensing devices 228, 230, 232, 234 shown in FIG. 2, such as an array of photodiodes. In an exemplary embodiment, each of the light-sensing devices detects a specific wavelength of light.

Embodiments of the invention may also include methods of using the apparatus as describe above or a light collection system. A light source may contact a target through an illumination funnel, sufficient to generate transmitted, transflected or reflected light. The transmitted, transflected or reflected light may enter a light collection system and be directed to one or more detectors, for example.

Thus, there has been shown and described several embodiments of a novel invention. As is evident from the foregoing description, certain aspects of the present invention are not limited by the particular details of the examples illustrated herein, and it is therefore contemplated that other modifications and applications, or equivalents thereof, will occur to those skilled in the art. The terms "have," "having," "includes" and "including" and similar terms as used in the foregoing specification are used in the sense of "optional" or "may include" and not as "required." Many changes, modifications, variations and other uses and applications of the present construction will, however, become apparent to those skilled in the art after considering the specification and the accompanying drawings. All such changes, modifications, variations and other uses and applications, which do not depart from the spirit and scope of the invention, are deemed to be covered by the invention, which is limited only by the claims that follow. It should be understood that the embodiments disclosed herein include any and all combinations of features described in any of the dependent claims

The invention claimed is:

1. An apparatus for concentrating light, the apparatus comprising:
    an first outer wall having an anterior end, a posterior end, an inner surface and an outer surface, the inner surface defining an interior portion, the interior portion having an anterior end and a posterior end;
    a light source disposed within the interior portion;
    wherein the first outer wall has an opening in the posterior end, the opening having an opening diameter;
    wherein the interior portion has a substantially frusto-conical shape;
    wherein the interior portion has a cross-sectional diameter at the opening equal to the opening diameter and a second cross-sectional diameter near the anterior end that is less than the opening diameter; and
    wherein the inner surface is photo-reflective.

2. The apparatus for concentrating light of claim 1, wherein the first outer wall includes metal, and the inner surface is polished.

3. The apparatus for concentrating light of claim 1, wherein the half angle of the frusto-conical shape from a perpendicular line bisecting the frusto-conical shape extending from the second cross-sectional diameter to the first cross-sectional diameter is less than about forty-five degrees.

4. The apparatus for concentrating light of claim 3, wherein the half angle of the frusto-conical shape is more than about five degrees and less than about twenty-five degrees.

5. The apparatus for concentrating light of claim 1, further comprising a condenser lens positioned underneath the opening for receiving light through a sample.

6. The apparatus for concentrating light of claim 5, wherein the condenser lens is an aspheric lens.

7. The apparatus for concentrating light of claim 5, further comprising an aperture located between the sample and the condenser lens.

8. The apparatus for concentrating light of claim 5, further comprising:
    a plurality of light filters;
    wherein each light filter of the plurality of light filters is positioned to receive light from the condenser lens and emit filtered light onto a corresponding photodetector of a plurality of photodetectors; and
    wherein each photodetector of the plurality of photodetectors is tuned to detect light in the spectrum emitted by the corresponding filter of the plurality of light filters.

9. The apparatus for concentrating light of claim 8, further comprising an aperture located between the sample and the condenser lens.

10. The apparatus for concentrating light of claim 5, further comprising a diffraction grating positioned underneath the condenser lens.

11. The apparatus for concentrating light of claim 10, further comprising an aperture located between the sample and the condenser lens.

12. The apparatus for concentrating light of claim 10, further comprising:
a plurality of light filters;
wherein each light filter of the plurality of light filters is positioned to receive light from the condenser lens and emit filtered light onto a corresponding photodetector of a plurality of photodetectors; and
wherein each photodetector of the plurality of photodetectors is tuned to detect light in the spectrum emitted by the corresponding filter of the plurality of light filters.

13. The apparatus for concentrating light of claim 1, further comprising:
a second outer wall having an anterior end, a posterior end, an inner surface and an outer surface, the inner surface defining an interior portion, the interior portion having an anterior end and a posterior end;
wherein the interior portion of the second outer wall having a first opening in the posterior end with a first cross-sectional diameter and the interior portion of the second outer wall having a second opening in the anterior end with a second cross-sectional diameter and the first cross-sectional diameter is greater than the second cross-sectional diameter;
wherein the interior portion has a substantially frusto-conical shape and is photo-reflective; and
wherein a sample can be positioned between the opening in the first outer wall and the second opening in the anterior end of the second outer wall.

14. The apparatus for concentrating light of claim 13, further comprising:
a plurality of light filters;
wherein each light filter of the plurality of light filters is positioned to receive light from the first opening in the posterior end of the second outer wall and emit filtered light onto a corresponding photodetector of a plurality of photodetectors; and
wherein each photodetector of the plurality of photodetectors is tuned to detect light in the spectrum emitted by the corresponding filter of the plurality of light filters.

15. A method for concentrating light, the method comprising:
utilizing a light source located within an interior portion of a first outer wall, wherein the first outer wall includes an anterior end, a posterior end, a photo-reflective inner surface and an outer surface, the inner surface defining an interior portion, the interior portion having a substantially frusto-conical shape, an anterior end and a posterior end, and the first outer wall has an opening in the posterior end, the opening having an opening diameter and the interior portion has a cross-sectional diameter at the opening equal to the opening diameter and a second cross-sectional diameter near the anterior end that is less than the opening diameter.

16. The method for concentrating light of claim 15, further comprising utilizing a condenser lens positioned underneath the opening for receiving light through a sample.

17. The method for concentrating light of claim 16, wherein the condenser lens is an aspheric lens.

18. The method for concentrating light of claim 16, further comprising utilizing an aperture located between the sample and the condenser lens.

19. The method for concentrating light of claim 16, further comprising:
utilizing a plurality of light filters, wherein each light filter of the plurality of light filters is positioned to receive light from the condenser lens and emit filtered light onto a corresponding plurality of photodetectors and each photodetector of the plurality of photodetectors is tuned to detect light in the spectrum emitted by the corresponding light filter of the plurality of light filters.

20. The method for concentrating light of claim 15, further comprising:
utilizing a second outer wall having an anterior end, a posterior end, an inner surface and an outer surface, the inner surface defining an interior portion, the interior portion is substantially frusto-conical shape, photo-reflective, and having an anterior end and a posterior end and the interior portion of the second outer wall having a first opening in the posterior end with a first cross-sectional diameter and the interior portion of the second outer wall having a second opening in the anterior end with a second cross-sectional diameter and the first cross-sectional diameter is greater than the second cross-sectional diameter; and
positioning a sample between the opening in the first outer wall and the second opening in the anterior end of the second outer wall.

21. The method for concentrating light of claim 20, further comprising:
utilizing a plurality of light filters, wherein each light filter of the plurality of light filters is positioned to receive light from the first opening in the posterior end of the second outer wall and emit filtered light onto a corresponding plurality of photodetectors and each photodetector of the plurality of photodetectors is tuned to detect light in the spectrum emitted by the corresponding light filter of the plurality of light filters.

22. The apparatus for concentrating light of claim 12, further comprising an aperture located between the sample and the condenser lens.

* * * * *